US009751812B2

(12) United States Patent
Bowers et al.

(10) Patent No.: US 9,751,812 B2
(45) Date of Patent: Sep. 5, 2017

(54) TAGGANT FOR CEMENT AUTHENTICATION

(71) Applicant: Elwha LLC, Bellevue, WA (US)

(72) Inventors: Jeffrey A. Bowers, Bellevue, WA (US); Bran Ferren, Beverly Hills, CA (US); W. Daniel Hillis, Encino, CA (US); Roderick A. Hyde, Redmond, WA (US); Jordin T. Kare, Seattle, WA (US); Cameron A. Myhrvold, Medina, WA (US); Conor L. Myhrvold, Medina, WA (US); Nathan P. Myhrvold, Medina, WA (US); Thomas J. Nugent, Jr., Bellevue, WA (US); Tony S. Pan, Cambridge, MA (US); Clarence T. Tegreene, Mercer Island, WA (US); David B. Tuckerman, Lafayette, CA (US); Lowell L. Wood, Jr., Bellevue, WA (US)

(73) Assignee: Elwha LLC, Bellevue, WA (US)

(*) Notice: Subject to any disclaimer, the term of this patent is extended or adjusted under 35 U.S.C. 154(b) by 503 days.

(21) Appl. No.: 14/292,334

(22) Filed: May 30, 2014

(65) Prior Publication Data

US 2015/0344376 A1    Dec. 3, 2015

(51) Int. Cl.
*C04B 28/02*    (2006.01)
*C04B 40/00*    (2006.01)
*G01N 33/38*    (2006.01)
*C04B 103/54*   (2006.01)

(52) U.S. Cl.
CPC .......... *C04B 40/0096* (2013.01); *C04B 28/02* (2013.01); *G01N 33/383* (2013.01); *C04B 2103/54* (2013.01)

(58) Field of Classification Search
CPC .......................... C04B 2103/54; G01N 33/383
See application file for complete search history.

(56) References Cited

U.S. PATENT DOCUMENTS

| 205,598 | A | * | 7/1878 | Willis | ..................... C04B 14/34 |
| | | | | | 106/643 |
| 4,131,064 | A | * | 12/1978 | Ryan | ..................... C06B 23/008 |
| | | | | | 102/293 |
| 4,209,302 | A | * | 6/1980 | Orelup | ................. C07D 295/13 |
| | | | | | 436/56 |
| 5,306,343 | A | * | 4/1994 | Richardson, III | .. C04B 40/0096 |
| | | | | | 106/273.1 |
| 5,451,505 | A | | 9/1995 | Dollinger | |
| 5,541,855 | A | | 7/1996 | Enzler et al. | |

(Continued)

OTHER PUBLICATIONS

Cryptography, from Wikipedia, the free encyclopedia (en.wikipedia.org/wiki/Cryptography#Modern_cryptography), retrieved on Aug. 11, 2014, 15 pages.

(Continued)

*Primary Examiner* — Paul West
*Assistant Examiner* — Mark A Shabman
(74) *Attorney, Agent, or Firm* — Foley & Lardner LLP (57) ABSTRACT

A traceable cement mixture includes a volume of cementitious material and a taggant disposed within the volume of cementitious material. The taggant includes data relating to a characteristic of the volume of cementitious material.

17 Claims, 6 Drawing Sheets

(56) References Cited

U.S. PATENT DOCUMENTS

| | | | | |
|---|---|---|---|---|
| 5,902,750 | A | * | 5/1999 | Fuerholzer ............. G01N 31/22 436/56 |
| 6,531,528 | B1 | * | 3/2003 | Kurp ....................... C04B 26/06 524/291 |
| 6,740,875 | B1 | | 5/2004 | Ishikawa et al. |
| 6,806,478 | B1 | | 10/2004 | Hatfield |
| 2009/0289765 | A1 | * | 11/2009 | Kaga ....................... B28B 23/00 340/10.1 |
| 2011/0138887 | A1 | * | 6/2011 | Targosz ................ G01N 33/42 73/61.42 |
| 2013/0104797 | A1 | * | 5/2013 | Chiappo ............. G01N 33/383 116/201 |

OTHER PUBLICATIONS

Gun Shoots DNA Bullets to Tag Criminals, from Discovery News (http://news.discovery.com/tech/biotechnology/gun-shoots-dna-bullets-tag-criminals-13012 . . . ), retrieved on Aug. 11, 2014, 5 pages.

* cited by examiner

TAGGANT FOR CEMENT AUTHENTICATION

BACKGROUND

Concrete is a mixture of cement and various other materials. The cement and other materials are often mixed at a concrete plant and transported (e.g., with concrete mixer trucks) to a jobsite. Concrete used in certain applications (e.g., for buildings, footings, etc.) may have a strength, ductility, or other characteristic that is specified by a customer, engineer, or still another person. The amount and grade of cement impacts the strength and other characteristics of the concrete. While certain characteristics of the concrete (e.g., slump, etc.) may be tested by an inspector, other characteristics (e.g., composition) may be more difficult to determine by an inspector in the field thereby making it difficult for an inspector to verify that the delivered concrete satisfies the identified specifications.

Traditionally, a driver delivers paperwork that identifies the composition and other characteristics of the concrete load (e.g., the identity of the mixing plant, etc.). Tracking a particular load requires monitoring the paperwork supplied by the driver. However, an inspector may not be able to independently authenticate various characteristics of the cement or the concrete (e.g., composition). The location of a particular concrete load may also be difficult for an inspector to track. Such load tracking may be particularly relevant during subsequent inspection of a structure after initial construction (e.g., during routine surveying, to determine the ability of a structure to withstand a storm or explosion, etc.). Despite these shortcomings, inspectors traditionally rely on paperwork provided upon delivery of the concrete load for initial authentication and subsequent inspection.

SUMMARY

One embodiment relates to a traceable cement mixture including a volume of cementitious material and a taggant disposed within the volume of cementitious material. The taggant includes data relating to a characteristic of the volume of cementitious material.

Another embodiment relates to a structure including a volume of concrete. The volume of concrete forms a base configured to interface with a ground volume. The volume of concrete includes a volume of cementitious material and a taggant disposed within the volume of cementitious material. The taggant includes data relating to a characteristic of the volume of concrete.

Still another embodiment relates to a cement authentication apparatus including a housing, a sensor, and a processor. The housing is configured to contain a volume of cementitious material having a taggant. The taggant includes data relating to a characteristic of the volume of cementitious material. The sensor is positioned to interface with the taggant and provide a sensor signal relating to the characteristic of the volume of cementitious material. The processor is configured to determine the characteristic of the volume of cementitious material by evaluating the sensor signal.

Yet another embodiment relates to a method of manufacturing a traceable cement mixture including providing a volume of cementitious material and positioning a taggant within the volume of cementitious material. The taggant includes data relating to a characteristic of the volume of cementitious material.

Another embodiment relates to a method of authenticating a cement mixture including scanning a volume of cementitious material for a taggant with a sensor. The method also includes sending or receiving data as a sensor signal with the sensor. The data relates to a characteristic of the volume of cementitious material. The method also includes determining the characteristic of the volume of cementitious material with a processor by evaluating the sensor signal.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The invention will become more fully understood from the following detailed description taken in conjunction with the accompanying drawings wherein like reference numerals refer to like elements, in which.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Taggants are intended to facilitate the authentication of a cementitious mixture. The taggants may be active (e.g., RFID, ultrasonic, etc.) and store authentication data or passive and be detected (e.g., with radiofrequency waves, with x-rays, etc.) to facilitate an authentication process. Active taggants may store energy (e.g., with a battery, etc.) or may be remotely powered (e.g., with an electromagnetic field, etc.). Such authentication reduces the risk that concrete having an improper composition will be used during construction. Authentication may ensure that a batch of concrete includes cement originating from an approved source. Taggants may be used to verify that the mix ratio of authenticated cement to other materials in a batch of concrete is within a specified range. Taggants also allow for the prospective or retrospective analysis of structures (e.g., buildings, bridges, etc.) to determine whether the appropriate concrete was poured during initial construction.

Figure 1:
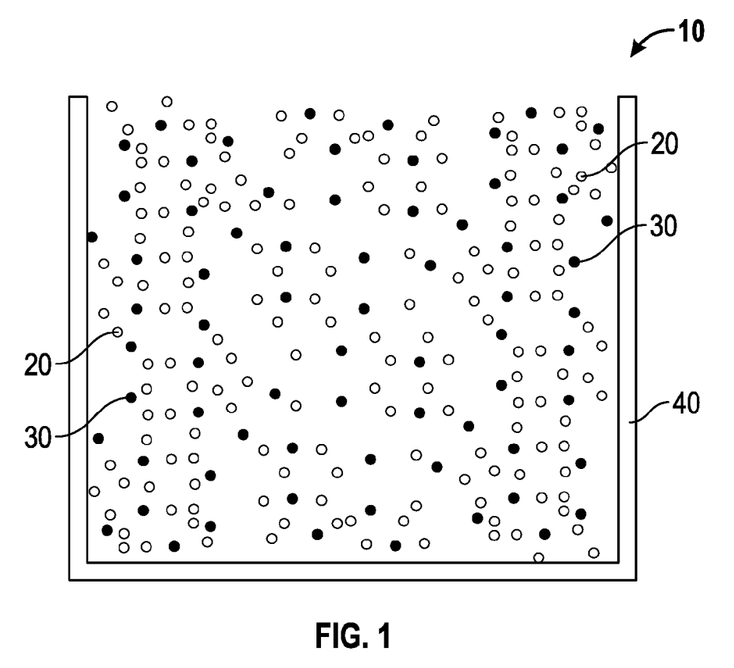
FIG. 1 is a side plan view of a traceable cement mixture, according to one embodiment.

Referring to the embodiment shown in FIG. 1, a mixture, shown as traceable cement mixture 10, includes cementitious material, shown as cement particles 20, and a taggant, shown as cement taggant 30. As shown in FIG. 1, traceable cement mixture 10 is disposed within a housing, shown as container 40. Container 40 may have a variety of shapes and may be rigid (e.g., made of rigid plastic, metal, etc.) or flexible (e.g., a plastic or paper bag, etc.). In other embodiments, container 40 is a portion of a machine used during the production of cement (e.g., a mix hopper, etc.).

As shown in FIG. 1, traceable cement mixture 10 includes a volume of cement particles 20. In one embodiment, cement particles 20 have a generally spherical shape. In other embodiments, cement particles 20 have another shape (e.g., ovular, discus, irregular, etc.). Cement particles 20 may be Portland cement composed primarily of hydraulic calcium silicates. In other embodiments, cement particles 20 may be another type of cement (e.g., a blended cement, another hydraulic cement, etc.) or still another material. Cement particles 20 may have a size of approximately 1 micron. In other embodiments, cement particles 20 are larger than one micron (e.g., 10 microns, 50 microns, 90 microns, etc.) or smaller than one micron (e.g., 0.5 microns, etc.). In use, cement particles 20 are hydrated (e.g., with water) and cure to form cured concrete. The shape, composition, size, and density of cement particles 20, among other characteristics, may impact the strength, hardness, toughness, or other features of the cured concrete. The shape, composition, size, or other feature of cement particles 20 may be specified (e.g., by a structural engineer, by a designer, by a regulatory agency, etc.) to produce concrete having specified characteristics (i.e. specified concrete).

Various manufactures may produce cement particles 20. According to one embodiment, mineral deposits are mined, and larger pieces are milled, ground, or otherwise processed to form cement particles 20. The manufacturer of cement particles 20 is tasked with producing cement particles 20 having the specified features. Such specified features may be identified as an acceptable range (e.g., a density of between 830 and 1650 kilograms per cubic meter), as a mean value (e.g., an average particle size of thirty microns, etc.), or as still another requirement. Some manufacturers may produce cement particles 20 having specified features that are outside the acceptable range or otherwise fail to conform with the identified requirements. By way of example, some manufacturers may lack the quality control processes, equipment, know-how, or other skills needed to produce cement particles 20 having specified features within the identified requirements. In other instances, some manufacturers may disingenuously produce cement particles 20 that fail to meet the identified requirements (e.g., by failing to sufficiently grind cement particles 20 as a cost cutting measure, by cutting cement particles 20 with other, non-specified types of cement, contaminants, other materials, etc.). As the particular features of cement particles 20 relate to the strength, hardness, toughness, or other features of the cured concrete, selection and verification of a particular manufacturer may impact the quality, life, strength, or other features of a structure.

Referring again to the embodiment shown in FIG. 1, cement taggants 30 are disposed within a volume of cement particles 20. Cement taggants 30 are intended to reduce the risk that improper cement particles 20 will be introduced into specified concrete. Cement taggants 30 are also intended to reduce the risk that cement particles 20 may be improperly processed or blended with other materials. In some embodiments, cement taggants 30 include data relating to a characteristic of the volume of cement particles 20. The characteristic of the volume of cement particles 20 may be a grade, a quality, a manufacturer, a manufacture date, an inspection status, an inspection date, an approval status, or still other properties. Cement taggants 30 may be introduced at various points during the manufacture and use of cement particles 20. In some embodiments, cement taggants 30 are introduced to traceable cement mixture 10 before the processing of the raw material (e.g., before cement particles 20 are formed through a grinding process, etc.). In other embodiments, cement taggants 30 are introduced to traceable cement mixture 10 after a cement particles 20 are processed (e.g., during a certification of cement particles 20, etc.) or after cement particles 20 are introduced into concrete, among other alternatives.

In one embodiment, cement taggant 30 is a discrete object that is configured to be individually monitored, handled, or examined. In other embodiments, cement taggant 30 is configured to be monitored, handled, or examined in aggregate with other cement taggants 30. By way of example, a scoop of cement taggants 30 may be monitored, handled, or examined as a group. Cement taggant 30 may have a size that is larger or smaller than one millimeter. In one embodiment, cement taggants 30 are nanoparticles and are configured to be monitored, handled, or examined in aggregate.

According to one embodiment, the size of cement taggant 30 corresponds with the size of cement particles 20. In still other embodiments, the density of cement taggant 30 corresponds with the density of cement particles 20. By way of example, cement taggant 30 may include a hollow shell having at least one of a specified weight and a specified volume such that the density of cement taggant 30 corresponds with the density of cement particles 20. Corresponding a feature (e.g., size, density, etc.) of cement taggant 30 with that of cement particles 20 reduces the risk that cement taggants 30 will separate from cement particles 20. By way of example, separation may otherwise occur during shipping, handling, due to an increase in viscosity of cement particles 20 post-hydration, or during another process. In other embodiments, the size, density, or other feature of cement taggants 30 is greater or less than the corresponding feature of cement particles 20 to encourage separation and facilitate detection of cement taggants 30 within traceable cement mixture 10. In still other embodiments, cement taggant 30 is configured to react with water such that a property (e.g., density, etc.) of cement taggant 30 changes to facilitate post-hydration separation. By way of example, cement taggant 30 may absorb more water than cement particles 20 and sink post hydration.

In some embodiments, cement taggants 30 are secured (e.g., the data is secured according to an encryption scheme). Securing cement taggants 30 is intended to reduce the risk of forgery of cement taggants 30. By way of example, a manufacturer may employ a certification process whereby an inspector evaluates cement particles 20. After authenticating the characteristic of cement particles 20, the inspector may introduce cement taggants 30 into a volume of cement particles 20. Securing cement particles 20 reduces the risk that the cement manufacturer, an intermediate party (e.g., a concrete mixing plant, a concrete transportation company, etc.), or still others will introduce cement taggants 30 into the volume of cement particles 20 or concrete produced therewith. In one embodiment, cement taggants 30 are secured and are configured to respond only to a specified request signal. An operator may retrieve the data only if the specified request signal is sent. If the operator does not know the specified request signal, cement taggants 30 may not respond at all or may not provide the data. In other embodiments, the data relating to the characteristic of cement particles 20 may be retrieved (e.g., read, etc.) only by those with a decryption key. In still other embodiments, cement taggants 30 have a specified feature intended to provide security. By way of example, cement taggants 30 may be difficult to produce (e.g., replicatable biological information encoded molecule taggants, specified isotopes, etc.). In still other embodiments, cement taggant 30 includes an RFID device that provides security. By way of example, the RFID device may employ an algorithm or provide a different code (e.g., number) based on a date or day of the week of interest (e.g., the manufacture date of cement particles 20, the mix date of cement mixture 10, etc.). By way of another example, the RFID device may employ an algorithm to provide a code that varies based upon still other inputs. While RFID devices are explicitly discussed herein, it should be understood that acoustic devices (e.g., ultrasonic devices, etc.) may provide similar functionality. Securing cement taggants 30 thereby facilitates distinguishing legitimate and illegitimate cement taggants 30 and also facilitates authenticating at least one of cement mixture 10 and cement particles 20.

In one embodiment, cement taggant 30 includes a storage device (e.g., a flash memory, a computer storage medium, etc.) having a memory configured to store the data. Such cement taggants 30 may include an integrated circuit to facilitate the storage or retrieval of the data from the memory. In some embodiments, the data is stored in the memory as ciphertext. Such ciphertext may vary based on the encryption scheme (e.g., symmetric-key, public key, etc.), the particular security protocol utilized, a date of encryption, or still other features of the encryption or data.

Cement taggants 30 have fluorescent properties, according to one embodiment. By way of example, cement taggant 30 may include a material having fluorescent properties, the material thereby configured to at least one of provide information and identify cement taggant 30 within the volume of cement particles 20. In one embodiment, the material is polymeric. Cement taggants 30 having fluorescent properties may facilitate the inspection of traceable cement mixture 10 or concrete produced therewith. In one embodiment, the material fluoresces when exposed to ultraviolet light. In other embodiments, the material fluoresces when exposed to electricity, heat, or still another form of energy. An inspector may authenticate a mixture by exposing the traceable cement mixture 10 or concrete produced therewith to an ultraviolet light and evaluating (e.g., visually, with a sensor, etc.) the presence of cement taggants 30 (e.g., the color, the intensity of the fluorescence, the number of cement taggants 30 present in the sample, etc.). By way of example, the color cement taggant 30 fluoresces may facilitate identifying a particular volume of concrete mixture 10, cement particles 20, or cement taggants 30. In other embodiments, cement taggants 30 are colored (e.g., painted, etc.) to and used to identify a particular volume of concrete mixture 10, cement particles 20, or cement taggants 30.

In some embodiments, different cement taggants 30 fluoresce different colors. The different colors may correspond to different characteristics of cement particles 20. By way of example, a blue fluorescence may indicate that the cement particles 20 were produced or mixed by a first manufacturer and a red fluorescence may indicate that the cement particles 20 were produced or mixed by a second manufacturer. In another embodiment, different color fluorescence may correspond to different grades of cement particles 20. While manufacturer identity and grades have been explicitly discussed, cement taggants 30 fluorescing with different colors may be used to distinguish between samples of cement particles 20 according to still other characteristics.

In some embodiments, cement taggants 30 are layered ceramic chips. The layered ceramic chips may have a size that is larger than one millimeter. The cement taggants 30 may include microprocessors and other devices (e.g., sensors, timers, etc.) configured to evaluate a property of cement particles 20 (e.g., moisture content, duration since processing, etc.). By way of example, cement taggant 30 may include a RFID device. Such a RFID device may be configured to interface with a sensing device to facilitate retrieval of the data (e.g., during an authentication process).

In other embodiments, cement taggant 30 includes a replicatable biological information encoded molecule, such as at least one of DNA and RNA. By way of example, cement taggant 30 may include a marker disposed within a capsule. The capsule may prevent degradation or dehydration of the marker when cement taggant 30 is introduced into the volume of cement particles 20. The replicatable biological information encoded molecule may be configured to fluoresce when exposed to a source of energy (e.g., ultraviolet light, electricity, heat, etc.). In some embodiments, the replicatable biological information encoded molecule or the organism containing the replicatable biological information encoded molecule is otherwise undetectable to an observer of traceable cement mixture 10. Fluorescing replicatable biological information encoded molecules may facilitate the inspection of traceable cement mixture 10 or concrete produced therewith. By way of example, the fluorescing replicatable biological information encoded molecule may facilitate an inspector's efforts to locate cement taggant 30 or may be used as a preliminary marker. According to another embodiment, the replicatable biological information encoded molecule itself encodes data (e.g., a code that is designed to indicate or store particular information). The replicatable biological information encoded molecule or the organism containing the replicatable biological information encoded molecule may be disposed within a material having a density different than the density of cement particles 20, or the replicatable biological information encoded molecule may be disposed within a capsule such that cement taggant 30 has a density different than the density of cement particles 20. In another embodiment, the replicatable biological information encoded molecule or the organism containing the replicatable biological information encoded molecule is positioned within a material having a density different than the density of water. Such materials may be organic materials, inorganic materials (e.g., foam, etc.), or hollow shells, among other alternatives. Replicatable biological information encoded molecule positioned within materials having a different density may float or sink within traceable cement mixture 10 or hydrated concrete. Such floating or sinking may facilitate the authentication of traceable cement mixture 10 or concrete produced therewith. According to another embodiment, cement taggant 30 includes a ferromagnetic material. Cement taggants 30 that include a ferromagnetic material may be extracted from cement mixture 10 with a magnetic field, thereby facilitating an authentication process involving removal or in-situ examination. In other embodiments, magnetized cement taggants 30 may be extracted using a non-magnetic material (e.g., iron, etc.). In still other embodiments, cement taggants 30 including a ferromagnetic material may be at least one of examined and detected using a magnetic field, the presence or response thereof authenticating cement mixture 10.

In still other embodiments, cement taggant 30 includes a material having a specified nuclear magnetic resonance spectrum. Such a material may absorb and re-emit electromagnetic radiation at a specific resonance frequency. The specific resonance frequency facilitates distinguishing cement taggant 30 from the various other materials within concrete (e.g., cement particles 20, aggregates, etc.) thereby facilitating authentication. In one embodiment, cement taggant 30 includes a trace element that may be electromagnetically, chemically, or otherwise detected. The trace element facilitates authentication by identifying cement taggant 30 within a volume of cement particles 20.

In another embodiment, cement taggant 30 includes an isotope configured to identify cement taggant 30 within a volume of cement particles 20. The isotope may be a Mossbauer active isotope that produces a Mossbauer spectrum when exposed to a corresponding gamma-ray source. By way of example, the isotope may be iron-57. The isotope may be mixed with cement particles 20 on a certain date (e.g., a manufacture date, a mix date, etc.). The isotope may be short lived and degrade at a particular rate. An inspector may evaluate the age of at least one of cement mixture 10 and cement particles 20 based on the ratios of the different isotopes therein. Accordingly, secured cement taggants 30 that include an isotope may be used to authenticate at least one of cement mixture 10 and cement particles 20.

According to another embodiment, cement taggant 30 includes a gamma-ray watermark having a combination of gamma-ray-emitting isotopes. Such gamma-ray watermarks are discussed in U.S. Pat. No. 6,740,875, granted on May 25, 2004, which is hereby incorporated by reference. A cement verification apparatus may include a sensor configured to interface with (e.g., detect, etc.) the electromagnetic radiation, the trace element, the Mossbauer spectrum, or the gamma-rays to identify cement taggant 30 within traceable cement mixture 10 or concrete produced therewith.

In some embodiments, cement taggant 30 changes upon exposure to a threshold level of water (e.g., exposed to any quantity of water, a specified humidity level, liquid water, etc.). In another embodiment, cement taggant 30 includes a RFID device configured to provide a response signal (e.g., to a request signal, etc.) that varies based on the moisture content of cement particles 20 or cement mixture 10. In other embodiments, moisture changes at least one of the optical spectrum (e.g., color, etc.), the infrared spectrum, and the nuclear magnetic resonance spectrum of cement taggant 30. The moisture content of cement may impact the strength, toughness, durability, or other features of concrete produced therewith. Where specified concrete is required, the moisture content of cement particles 20 must be controlled. While cement particles 20 may be dried to a preferred moisture content during initial manufacture (e.g., in a drying oven, etc.), subsequent storage may expose cement particles 20 to moisture. By way of example, storage outside of a climate-controlled environment (e.g., outside, etc.) exposes cement particles 20 to liquid water (e.g., due to rain) and water vapor (e.g., due to humidity in the surrounding air). Such subsequent storage may increase the moisture content of cement particles 20 and change a property of concrete produced therefrom (e.g., strength, toughness, etc.). The moisture content of cement particles 20 may also be greater than a preferred level due to insufficient drying during initial manufacture. A greater-than-preferred moisture content of cement particles 20 may be difficult to observe. While re-testing may occur when cement particles 20 are isolated (e.g., prior to mixing), determining the moisture content of cement particles 20 after hydrating and mixing the concrete may be difficult. Cement taggants 30 that change (e.g. permanently, temporarily, etc.) when exposed to water facilitates the authentication of cement particles 20. By way of example, an inspector may evaluate cement taggants 30 (e.g., pre-hydration, within hydrated concrete, etc.) to determine whether cement particles 20 have been exposed beyond a threshold level.

According to one embodiment, cement taggant 30 includes a property that degrades at a specific rate in the presence of water. By way of example, the property of cement taggant 30 may be density, size, or magnetic permeability. In one embodiment, cement taggants 30 are introduced to cement particles 20 during initial manufacture, and the magnetic permeability of cement taggant 30 degrades as cement taggant 30 is exposed to water. Cement taggants 30 may include iron, and the magnetic permeability may change due to oxidation or reduction (i.e. the magnetic permeability of cement taggant 30 may degrade due to rusting) or by still another mechanism. Subsequent evaluation of the magnetic permeability of cement taggant 30 thereby allows an inspector to determine a water exposure level for cement particles 20.

In another embodiment, cement taggant 30 includes a material that changes color when exposed to a threshold level of water (e.g., exposed to any quantity of water, a specified humidity level, liquid water, etc.). Such a color change may occur due to oxidation or reduction. By way of example, cement taggant 30 may include iron, which changes color as it rusts. In other embodiments, the material includes a water-sensitive dye configured to change color when exposed to water. In one embodiment, cement taggants 30 configured to change color are introduced to cement particles 20 during initial manufacture.

The exposure to water needed to produce the color change may be specified. The specified exposure may be identified in terms of at least one of a time, a threshold humidity, or another measurement of exposure. After the period of time, in the presence of the threshold humidity, or as the exposure condition occurs, the material changes color. The change in color may be binary (e.g., white below the threshold and red above the threshold, etc.) or may occur gradually (e.g., initially white, pink after thirty days, and red after sixty days). In some embodiments, the color change varies based on both the intensity of exposure (e.g., humidity in the air, liquid water, etc.) and based on the duration of exposure (i.e. the time cement taggant 30 is exposed to the particular intensity of water). An inspector may evaluate cement taggants 30 (e.g., pre-hydration, etc.) to determine whether cement particles 20 have been exposed beyond a threshold level. Such evaluation may occur visually (e.g., traceable cement mixture 10 is red, thereby indicating excess exposure to water or humidity, etc.) or may occur through the use of a sensor (e.g., an image sensor) and a processor configured to evaluate a sensor signal from the sensor, determine the color of traceable cement mixture 10 or cement taggants 30, and correspond the color with a level of exposure to water.

Figure 2:
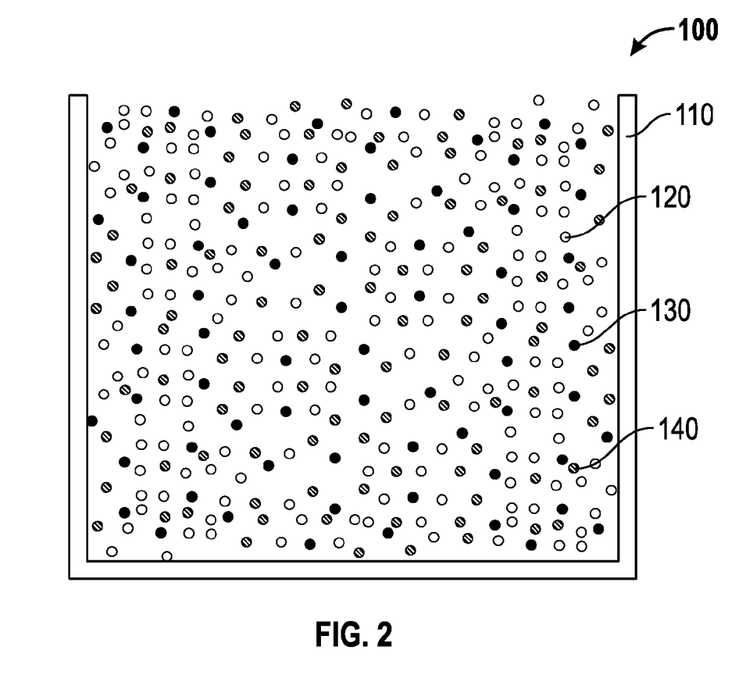
FIG. 2 is a side plan view of a traceable cement mixture, according to another embodiment.

Referring next to the embodiment shown in FIG. 2, a mixture, shown as cement mixture 100, is positioned within a housing, shown as container 110. As shown in FIG. 2, cement mixture 100 includes cementitious material, shown as cement particles 120, a plurality of taggants, shown as cement taggants 130, and an additional material, shown as supplementary particles 140. Supplementary particles 140 may include aggregates, a reinforcement fiber, a chemical admixture, a mineral admixture (e.g., fly ash, sand, etc.), unauthenticated cement (i.e. wild cement), or still other materials. In one embodiment, taggants are added to supplementary particles 140 to indicate the presence thereof. Cement mixture 100 may be formed by mixing a volume of supplementary particles 140 with cement taggants 130 and a volume of cement particles 120. According to an embodiment, the volume of supplementary particles 140 mixed with the volume of cement particles 120 is specified, the ratio forming an additional material mix ratio. The amount of supplementary particles 140 relative to cement particles 120 may impact the strength of the concrete. A volume of cement taggants 130 may be disposed within the volume of cement particles 120 according to a taggant mix ratio.

In some embodiments, an amount (e.g., volume, number, etc.) of cement taggants 130 are added according to the taggant mix ratio during the initial manufacture of cement particles 120 (e.g., upon grinding, upon authentication, etc.). The amount of cement taggants 130 added to cement particles 120 may be associated with the quality of the cement (e.g., more cement taggants 130 may be added to premium cement while fewer cement taggants 130 may be added to standard quality cement, etc.). Such a mixture of cement taggants 130 and cement particles 120 may form a traceable cement mixture. Supplementary particles 140 may be later introduced to the traceable cement mixture. In some embodiments, supplementary particles 140 are wild cement, the wild cement having properties (e.g., moisture content, size, shape, grade, etc.) that reduce the cost of supplementary particles 140 relative to cement particles 120. Authenticating a cement mixture may include monitoring the taggant mix ratio to determine a dilution of tagged cement with wild cement. Supplementary particles 140 may be introduced into cement particles 120 during a mixing operation either inadvertently (e.g., a mixing plant may accidentally add grades of cement or other materials that are inappropriate for the specified concrete) or disingenuously (e.g., a mixing plant may add filler materials to increase the volume of concrete produced).

Specified concrete includes a preferred ratio of cement. Introducing cement taggants 130 according to the taggant mix ratio establishes a specified amount (e.g., volume, number, etc.) of cement taggants 130 that should be present within the specified concrete. A specified concrete including the preferred ratio of cement but less than the specified amount of cement taggants 130 suggests the introduction of supplementary particles 140.

Strength testing, hardness testing, or observation of the mixing process, among other alternatives, may be used to verify that the specified concrete includes the preferred ratio of cement. An authentication process may be used to determine whether the specified concrete includes a sufficient amount of cement taggants 130. The observed amount of cement taggants 130 within a volume of cement particles (i.e. cementitious material that has not been mixed) may be compared with a specified amount of cement taggants 130 (e.g., according to the taggant mix ratio used during authentication) to verify that supplementary particles 140 have not been introduced. According to one embodiment, a processor of an authentication apparatus is configured to compare the observed amount of cement taggants 130 with the specified amount. The processor may provide a confirmation signal when or if the observed amount of cement taggants 130 reaches or exceeds the specified amount of cement taggants 130. In some embodiments, cement taggants 130 include a material that fluoresces, and the amount of cement taggants 130 may be determined by counting or otherwise measuring the fluorescence. In other embodiments, the cementitious material or concrete is otherwise evaluated (e.g., with scanning, through resonance imaging, etc.) to determine the amount of cement taggants 130 therein.

In one embodiment, cement mixture 100 includes a first taggant including data relating to a characteristic of cement particles 120 and a second taggant including different data relating to a characteristic of cement particles 120. The data of the first taggant and the second taggant may relate to the same or different characteristics of cement particles 120. By way of example, the first taggant may include data relating to an inspection status of cement particles 120 (e.g., inspected but did not meet specifications) and the second taggant may also include data relating to an inspection status of cement particles 120 (e.g., inspected and met specifications). Verification of the mixture may occur by scanning for taggants including data indicating that cement particles 120 were authenticated and met specifications.

In another embodiment, the first taggant includes data relating to the manufacturer of cement particles 120, and the second taggant includes data relating to the manufacturing date of cement particles 120. Taggants having data relating to different characteristics facilitates gathering more information during a subsequent authentication of cement particles 120 (e.g., by an inspector, etc.). According to one embodiment, cement taggants 130 include one piece of data. According to another embodiment, cement taggants 130 include multiple pieces of data. Including multiple pieces of data may facilitate subsequent verification efforts (e.g., an inspector may determine information about different characteristics of cement particles 120 from a single cement taggant 130). In still other embodiments, the ratio of the first taggant to the second taggant may code information (e.g., premium cement may have more of a first taggant, etc.). By way of example, a manufacturer may begin a period by adding a first taggant (e.g., a taggant including platinum such that an x-ray spectrum having a recognizable feature is produced, etc.) and incrementally (e.g., each day, each week, etc.) adding more of a second taggant (e.g., a taggant including rhodium such that an x-ray spectrum having a recognizable feature is produced, etc.), the ratio of the two taggants (e.g., a ratio of the two materials as indicated by the x-ray spectrum, etc.) relating to the date of manufacture.

In some embodiments, the first taggant and the second taggant include the same identification mechanism (i.e. both taggants are the same type). By way of example, the first taggant and the second taggant may be RFID devices or taggants that are responsive to x-rays. Such taggants may include or be configured to provide different data (e.g., the first taggant may indicate the manufacture name and the second taggant may indicate the date of manufacture, etc.). In other embodiments, the first taggant is a different type of identification device than the second taggant. By way of example, the first taggant may include at least one of a fluorescent material, a nanoparticle, a RFID device, a replicatable biological information encoded molecule, a material having a specified nuclear magnetic resonance spectrum, a trace element, an particular isotope, and a gamma-ray watermark whereas the second taggant may include another of a fluorescent material, a nanoparticle, a RFID device, a replicatable biological information encoded molecule, a material having a specified nuclear magnetic resonance spectrum, a trace element, an particular isotope, and a gamma-ray watermark. In one embodiment, the first taggant includes an RFID device, an x-ray type tag, or another type of taggant that may be examined after the concrete has set whereas the second taggant includes a replicatable biological information encoded molecule or another type of taggant that may be examined before the concrete has set. In another embodiment, the first taggant includes an additive (e.g., manganese, etc.) that is detectable within a spectrum (e.g., an x-ray spectrum) to identify a first piece of data (e.g., manganese may be associated with a particular manufacture of cement), and the second taggant may include an additive (e.g., platinum, etc.) that is detectable within a spectrum to identify a second piece of data (e.g., to indicate a premium grade cement, etc.). A single taggant may include both pieces of data, according to an alternative embodiment. In other embodiments, at least one of a plurality of identification mechanisms is different between the first taggant and the second taggant.

Figure 3:
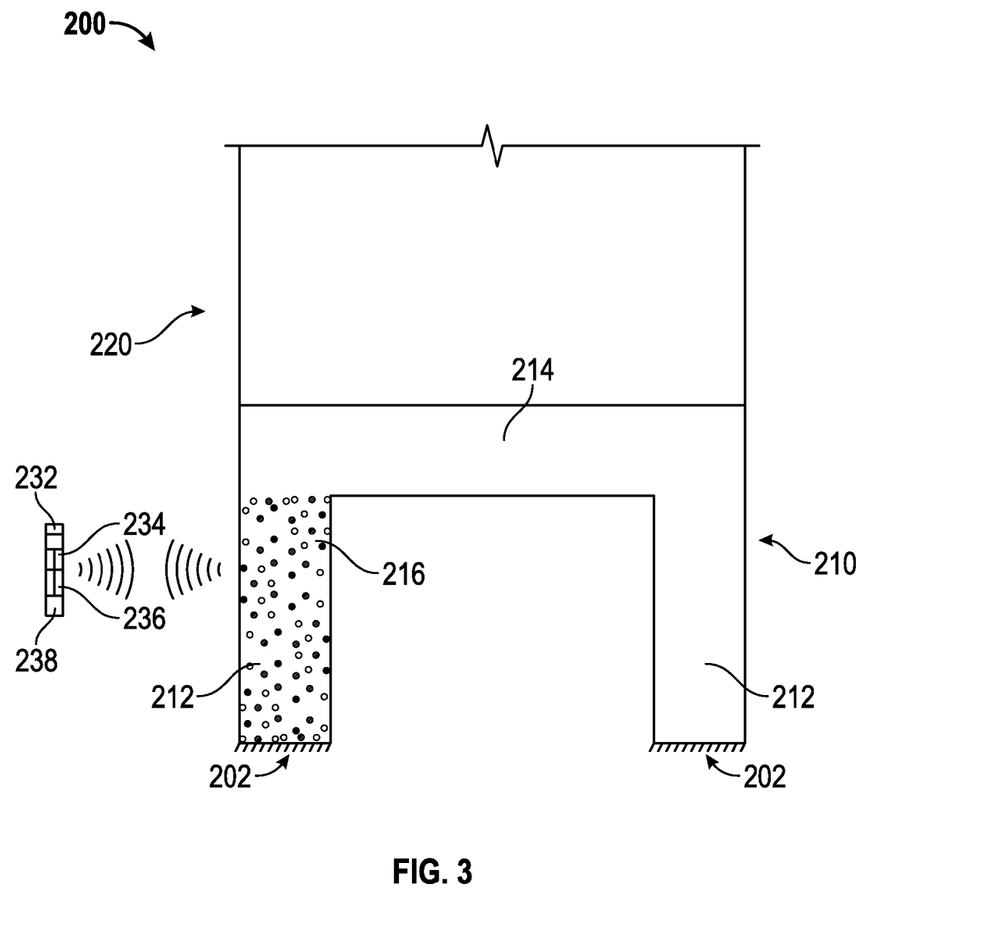
FIG. 3 is a side plan view of a building including a concrete base, according to one embodiment.

Referring next to the embodiment shown in FIG. 3, a structure, shown as building 200, includes a base, shown as footing 210, and a supported portion, shown as elevated portion 220. As shown in FIG. 3, footing 210 includes a column 212 and a lateral support portion 214. While shown in FIG. 3 as having two columns 212 coupled by lateral support portion 214, building 200 may be otherwise shaped. In one embodiment, footing 210 includes concrete and a reinforcing material (e.g., rebar, etc.). Columns 212 interface with a ground volume, shown as ground surface 202. Footing 210 supports elevated portion 220. The weight of elevated portion 220, forces due to wind acting on elevated portion 220, forces due to seismic activity, and still other loads may be imparted on footing 210.

In one embodiment, footing 210 is manufactured from authenticated concrete to reduce the risk that an inappropriate concrete mixture (e.g., inferior concrete) may be relied upon to support the loads imparted on footing 210. As shown in FIG. 3, concrete including a taggant, shown as cement taggants 216, is shaped (e.g., poured into forms, assembled using pre-formed concrete components, etc.) to produce footing 210. Cement taggants 216 may remain within footing 210 during the life of building 200, as shown in FIG. 3. In some embodiments, all of the concrete within footing 210 includes cement taggants 216. In other embodiments, only a portion of the concrete within footing 210 includes cement taggants 216 (e.g., concrete within columns 212, etc.). While footing 210 is explicitly discussed herein, still other portions of building 200 may be manufactured from concrete that includes cement taggants 216 (e.g., elevator shafts, floor support beams, other structural components, etc.).

In some embodiments, different portions of building 200 are manufactured from concrete and include different cement taggants 216. Different cement taggants 216 may identify different portions of building 200. By way of example, cement taggants 216 may include an RFID device that responds (e.g., to a request signal) with a design location for the corresponding concrete (i.e. a floor or portion of the building for which the concrete should have been or should be poured). An inspector may scan the concrete before pouring to verify that the concrete will be poured into a form for the appropriate portion of the building. An inspector may also scan the concrete after the concrete is poured (e.g., during a subsequent investigation where a portion of the building has failed) and retrieve the design location for the concrete to verify that the appropriate concrete was poured in the appropriate location. Such identification may reduce the risk that a particular portion of building 200 may be manufactured from concrete having properties other than those specified (e.g., by an architect or engineer, etc.). By way of example, concrete for columns 212 may have a characteristic (e.g., strength, grade, quality, manufacturer, manufacture date, inspection status, approval status, etc.) that is different than the characteristic of concrete for lateral support portion 214. In one embodiment, column 212 includes concrete having a characteristic that is specified to facilitate compressive loading wherein lateral support portion 214 includes concrete having a characteristic that is specified to facilitate bending loading. Cement taggants 216 include data identifying such characteristics. In one embodiment, cement taggants 216 reduce the risk of applying (e.g., inadvertently, disingenuously, etc.) concrete intended to carry compressive loading in columns 212 at locations exposed primarily to bending stresses (e.g., lateral support portion 214). The concrete of footing 210 may be authenticated by cement taggants 216 in-situ (e.g., data on cement taggants 216, the presence of cement taggants 216, the amount of cement taggants 216, etc.).

Referring again to the exemplary embodiment shown in FIG. 3, a cement authentication apparatus, shown as scanner 230, interfaces with cement taggants 216 to determine a characteristic of the concrete in footing 210. In one embodiment, scanner 230 is used to authenticate the composition, history, grade, or other characteristic of concrete in-situ (i.e. in position within footing 210). The authentication of the concrete may be accomplished non-invasively (i.e. without sampling, coring, or otherwise removing the concrete from footing 210). Non-invasive testing of footing 210 is intended to collect data without risking damage to building 200 or requiring subsequent concrete repair.

In one embodiment, scanner 230 is used to proactively determine buildings 200 that may be at risk for damage (e.g., due to a potential or anticipated storm, due to potential or historical seismic loading, etc.). By way of example, a risk factor may be associated with building 200 based on a feature of cement taggants 216 (e.g., an amount of cement taggants 216, data in cement taggants 216, etc.). The risk factor may correspond to a potential for damage due to wind, seismic, or other types of loading. In another embodiment, scanner 230 is used as part of an investigation into potential causes for damage to building 200. Cement taggants 216 remain within the concrete and remain readable even after an extended period of time. By way of example, cement taggants 216 may identify a manufacturer even after jobsite records have been discarded or as part of an authentication process during initial construction. Cement taggants 216 may include materials (e.g., polymers, etc.) selected to reduce the risk of damage (e.g., during collapse of a building). In other embodiments, cement taggants 216 are disposed within and protected by concrete thereby reducing the risk of damage during collapse of a building. In other embodiments, scanner 230 may be used to inspect footing 210 to verify the quality of the concrete. By way of example, scanner 230 may be used to identify voids in concrete by scanning for taggants. In still other embodiments, scanner 230 may be used to identify a particular portion of building 200 from which a sample of material was taken (e.g., scanner 230 may separate the concrete of upper floors from the concrete of lower floors, etc.).

As shown in FIG. 3, scanner 230 includes a housing, shown as body 232, at least partially surrounding a generator 234. Generator 234 is configured to produce an interrogation signal, according to an embodiment. In some embodiments, generator 234 produces a radio frequency wave (e.g., to interface with cement taggants 216 having RFID devices). In other embodiments, generator 234 is a gamma-ray source (e.g., to interface with cement taggants 216 having particular isotopes, etc.). In still other embodiments, generator 234 is a neutron generator configured to interrogate taggant 216 and trigger a response spectrum. In still other embodiments, the interrogation signal may include an x-ray, an ultraviolet wave, or an acoustic wave. By way of example, cement taggants 216 may respond to the acoustic wave and provide authenticating information (e.g., resonate at a particular frequency, scatter the acoustic wave according to a specified pattern to provide authentication information, store energy from a probe signal and provide a response signal, etc.).

In one embodiment, generator 234 is positioned to direct the interrogation signal toward footing 210. In another embodiment, a waveguide directs the interrogation signal from generator 234 toward footing 210. Scanner 230 may further include a sensor 236 positioned to receive response signal (e.g., an electromagnetic wave produced by cement taggant 216, an electromagnetic wave re-radiated or reflected from cement taggant 216, etc.). A processor 238 is configured to evaluate the interrogation signal produced by generator 234 and the response signal received by sensor 236 to determine a characteristic of the cement within footing 210 (e.g., pour quality, strength, grade, quality, manufacturer, manufacture date, inspection status, approval status, etc.).

In another embodiment, scanner 230 does not include generator 234. Processor 238 of scanner 230 may be configured to evaluate response signals produced by cement taggants 216 (e.g., cement taggants 216 including RFID devices, light waves produced by fluorescent cement taggants 216, etc.), identify a trace element of cement taggant 216, or otherwise interact with cement taggants 216. Such interaction may facilitate the retrieval of data or determine the amount (e.g., quantity, density, presence, etc.) of cement taggants 216 within footing 210.

Figure 4:
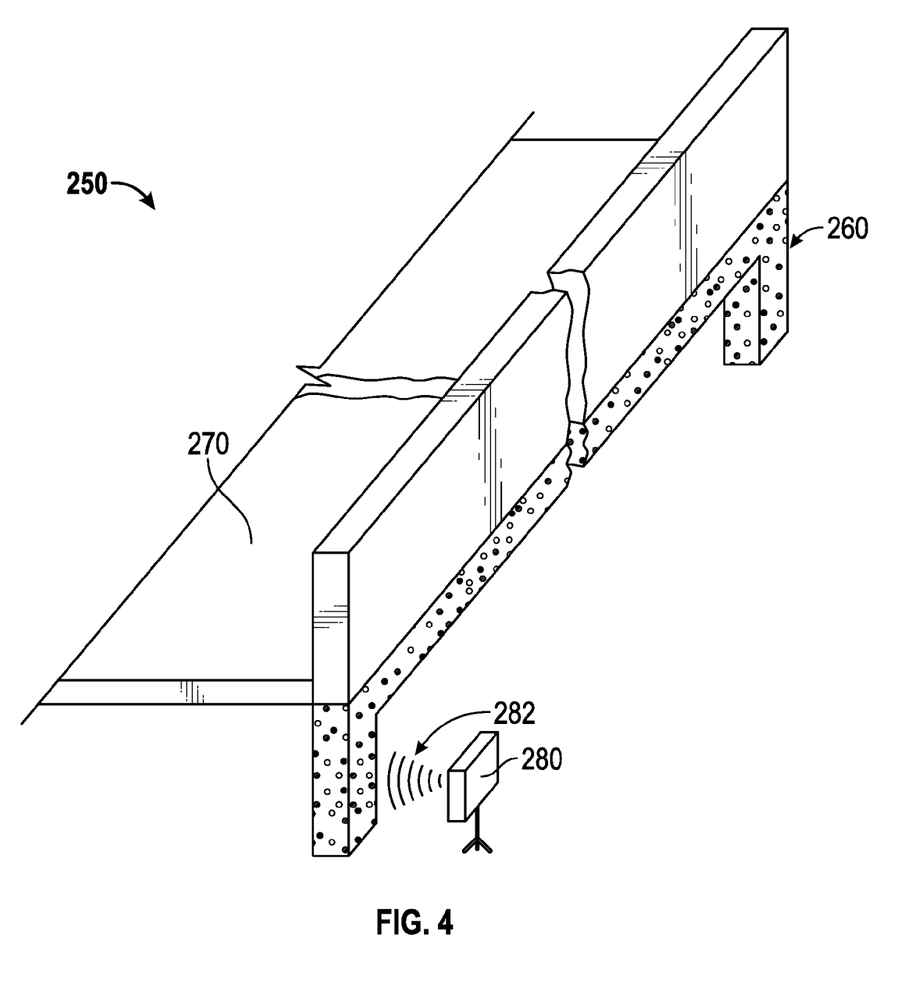
FIG. 4 is a side plan view of a bridge including a concrete base, according to one embodiment.

Referring next to the embodiment shown in FIG. 4, a structure, shown as bridge 250, includes a base, shown as footing 260, and a supported portion, shown as roadway 270. Footing 260 may include concrete having specified characteristics (e.g., strength, grade, quality, manufacturer, manufacture date, inspection status, approval status, etc.). Roadway 270 may include concrete or may include another material (e.g., asphalt, gravel, etc.). As shown in FIG. 4, a cement authentication apparatus, shown as scanner 280, is used to authenticate the concrete of footing 260. Scanner 280 may direct interrogation signals 282 toward footing 260. In other embodiments, scanner 280 otherwise interfaces with footing 260 to retrieve data or determine the amount (e.g., quantity, density, presence, etc.) of taggants within footing 260. Scanner 280 facilitates post-pour inspection of bridge 250 and reduces subsequent reliance on jobsite records to determine characteristics of the cement. In one embodiment, taggants within footing 260 have properties that facilitate post-pour interrogation thereof. By way of example, the taggants may have a RFID device or may be a gamma-ray-sensitive device such that data encoded therein may be retrieved even if the surface of footing 260 is covered (e.g., covered with soil or gravel, etc.). In other embodiments, the taggants are infra-red sensitive or fluoresce and are configured to facilitate examination thereof when the surface of footing 260 is visible or accessible.

Figure 5:
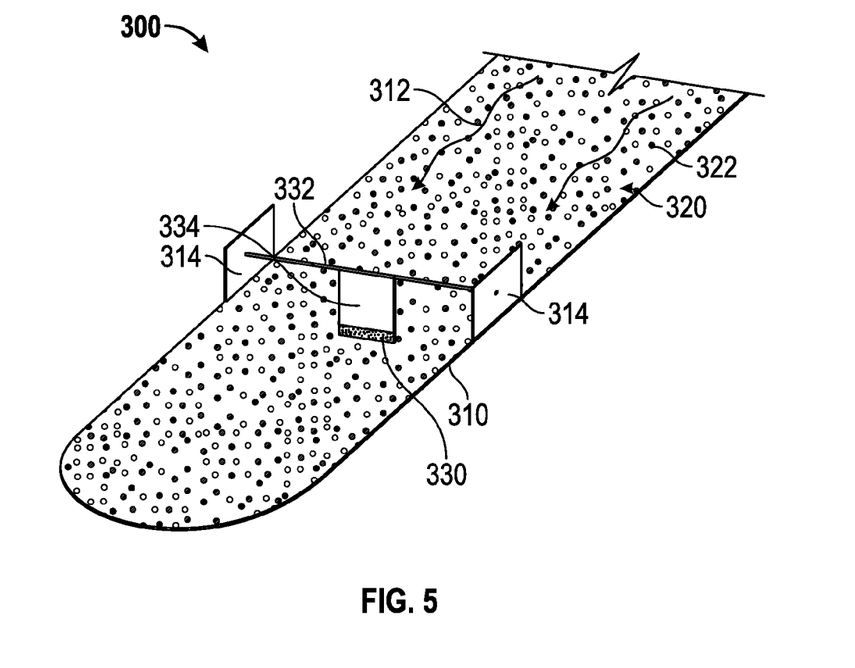
FIGS. 5-6 are isometric views of a cement authentication apparatus, according to two embodiments.
Figure 6:
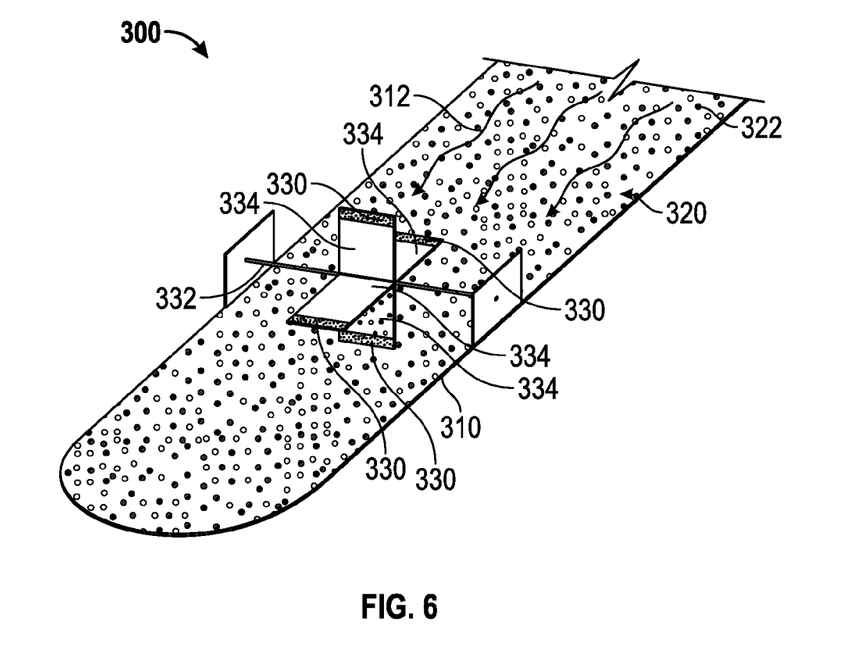
Figure 7:
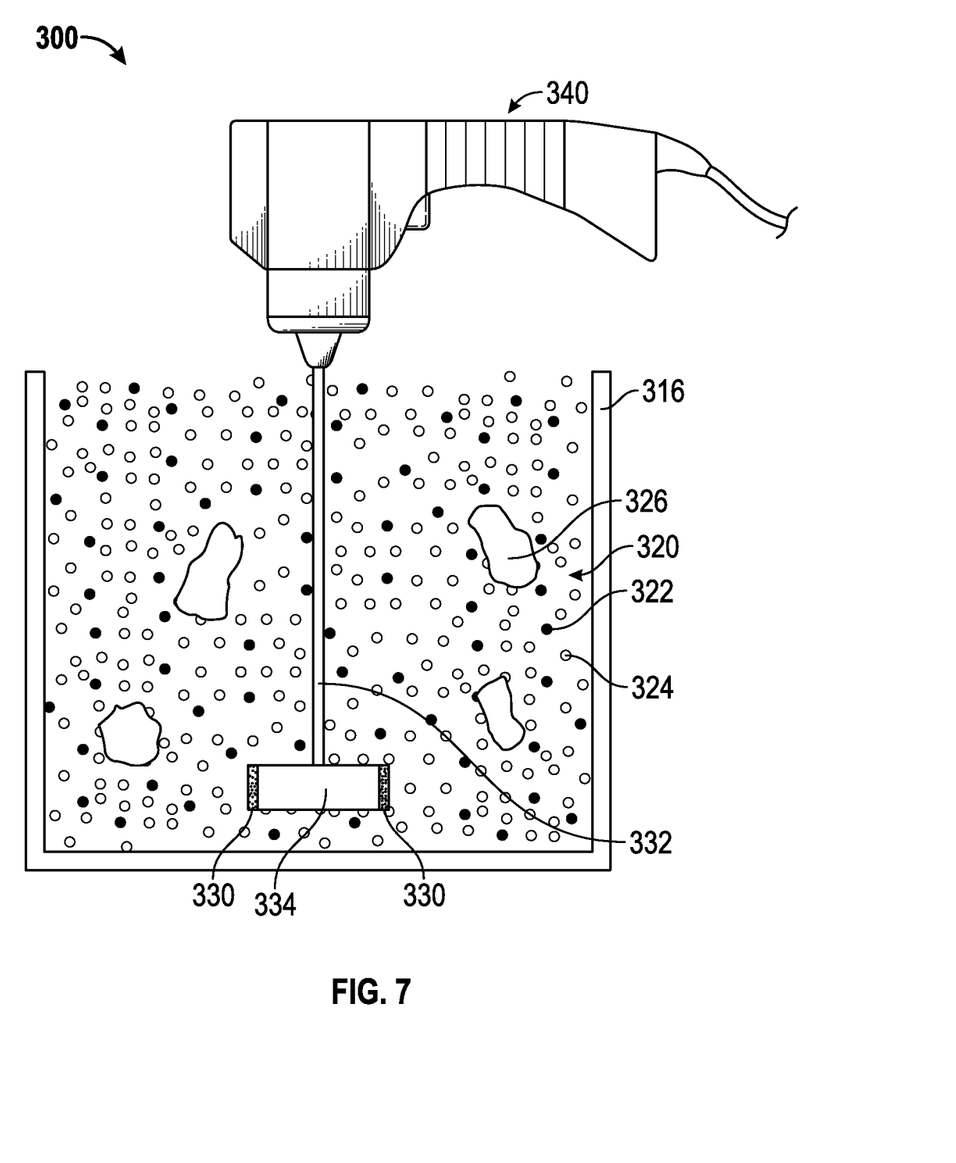
FIG. 7 is a side plan view of a cement authentication apparatus, according to another embodiment.

Referring next to FIGS. 5-7, a cement authentication apparatus may be used to determine a characteristic of cement. As shown in FIGS. 5-6, a cement authentication apparatus, shown as authentication assembly 300, includes a housing, shown as chute 310. Chute 310 is configured to contain a volume of cementitious material, shown as concrete 320, that includes a taggant, shown as cement taggant 322. In some embodiments, chute 310 is a concrete chute for a concrete mixer truck. The other components of authentication assembly 300 may be fixed or removably coupled to chute 310. By way of example, an inspector may couple chute 310 to the concrete mixer truck at a jobsite to authenticate concrete 320. Such authentication may occur for each concrete mixer truck or with a sample of concrete mixer trucks (e.g., one truck within a group of trucks, etc.).

Concrete 320 may include a mixture of cement and additional materials or may include only cementitious material and cement taggants 322. Concrete 320 may be dry (e.g., cement powder and other materials, etc.) or may be wet (e.g., a mixture of cement powder, other materials, and water, etc.).

In one embodiment, concrete 320 flows within chute 310 along flow direction 312. As shown in FIGS. 5-6, a sensor 330 is positioned to interface with cement taggant 322. Sensor 330 may detect response signals (e.g., light waves, radio waves, gamma rays, etc.) produced by cement taggant 322 within concrete 320. In other embodiments, sensor 330 otherwise interfaces with cement taggants 322 to detect data or the amount of cement taggants 322 within concrete 320. According to one embodiment, sensor 330 is configured to provide a sensor signal relating to a characteristic of concrete 320. In some embodiments, sensor 330 provides a plurality of sensor signals at a sampling rate. Authentication assembly 300 may include a processor configured to determine the characteristic of concrete 320 by evaluating the sensor signal, according to an exemplary embodiment. The processor may be configured to evaluate the plurality of sensor signals to authenticate an entire batch of concrete 320, average data from the plurality of sensors signals, or evaluate the amount of cement taggants 322 within different portions of concrete 320 (e.g., an amount of cement taggants 322 during the initial pour relative to a mid-pour amount of cement taggants 322), among other alternatives.

In some embodiments, authentication assembly 300 includes a flow rate sensor configured to provide flow rate signals relating to the flow rate of concrete 320 along chute 310. The processor may be configured to determine the characteristic of cement within concrete 320 by evaluating the flow rate signals. By way of example, the processor may divide the amount of cement taggants 322 detected by sensor 330 in a period of time by the flow rate of concrete 320 to estimate the total number of cement taggants 322 within a batch of concrete 320.

In one embodiment, cement taggants 322 are positioned within a hollow shell (e.g., a polymeric shell, etc.) or include a material having a density that is less than the density of concrete 320. As shown in FIG. 5, sensor 330 is coupled to a rod 332 with a fin 334. In some embodiments, rod 332 is rotatably coupled to brackets 314 of chute 310 and defines an axis of rotation. Concrete 320 flowing along chute 310 contacts fin 334 and rotates rod 332 about the axis of rotation and relative to brackets 314. As shown in FIG. 5, sensor 330 is positioned at an end of fin 334 such that rotation of fin 334 and rod 332 positions sensor 330 along an upper surface of concrete 320 (e.g., to interface with a greater amount of cement taggants 322 floating along an upper surface of concrete 320, etc.).

In another embodiment, rod 332 is fixed to brackets 314 such that fin 334 remains stationary relative to chute 310. Cement taggants 322 interface with sensor 330 as concrete 320 flows within chute 310. Authentication assembly 300 having a stationary fin 334 positions sensor 330 within the volume of concrete 320 (e.g., thereby interfacing with cement taggants 322 having a density equal to or greater than the density of concrete 320). In some embodiments, authentication assembly 300 includes a fixed or rotating fin 334 to selectively interface with cement taggants 322 having particular data. By way of example, concrete 320 may include a first set of cement taggants 322 having a first density and a second set of cement taggants 322 having a second density. Authentication assembly 300 may include a rotating fin 334 to position sensor 330 for interfacing with either the first set of cement taggants 322 or the second set of cement taggants 322. In still other embodiments, fin 334 is fixed (e.g., within a plane orthogonal to flow direction 312), and a plurality of sensors 330 interface with cement taggants 322. A first sensor 330 may be positioned to interface with the first set of cement taggants 322 (e.g., along the surface of concrete 320, etc.), and a second sensor 330 may be positioned to interface with the second set of cement taggants 322 (e.g., at an end of fin 334, etc.).

Referring to the embodiment shown in FIG. 6, authentication assembly 300 includes a plurality of sensors 330 coupled to rod 332 with a plurality of fins 334. In one embodiment, the plurality of sensors 330 provide a plurality of sensor signals. A processor may evaluate the plurality of sensor signals to determine the characteristic of concrete 320. Concrete 320 flowing along flow direction 312 rotates fins 334 thereby sequentially exposing sensors 330 to concrete 320. According to one embodiment, sensors 330 are identical and the processor is configured to average or otherwise manipulate signals from sensors 330 (e.g., to reduce the risk of false negative readings from one sensor 330). According to another embodiment, sensors 330 detect different cement taggants 322 (e.g., a first sensor 330 is a photo sensor to detect the fluorescence of cement taggants 322 and a second sensor is a radiofrequency antenna configured to receive radio waves from cement taggants 322, etc.).

Referring next to the embodiment shown in FIG. 7, concrete 320 is positioned within a housing, shown as container 316. In one embodiment, an inspector authenticates concrete 320 by positioning a sample in container 316 and operating authentication assembly 300. As shown in FIG. 7, concrete 320 includes cement taggants 322, a volume of cementitious material, shown as cement particles 324, and additional material, shown as aggregate 326. Sensors 330 are coupled to a driver, shown as drill 340, with rod 332 and fin 334. Drill 340 moves (e.g., rotates, etc.) rod 332 and fin 334 within concrete 320. A processor is configured to evaluate sensor signals provided by sensors 330 to determine a characteristic of concrete 320. As shown in FIG. 7, authentication assembly 300 may authenticate wet or dry concrete 320. In some embodiments, concrete 320 does not flow through container 316 thereby reducing the need to couple authentication assembly 300 along the flow path between the batch of concrete (e.g., within a drum of a concrete mixer truck, etc.) and work area (e.g., a concrete form). Authentication assembly 300 as shown in FIG. 7 is intended to facilitate the remote authentication of concrete 320 (e.g., within a dedicated test area on a jobsite, etc.). In other embodiments, sensor 330 is positioned outside the volume of concrete 320. Sensor 330 may authenticate concrete 320 by interfacing with cement taggants 322 therein (e.g., by sensing response signals generated by cement taggants 322, by identifying the trace elements of cement taggants 322, etc.).

Figure 8:
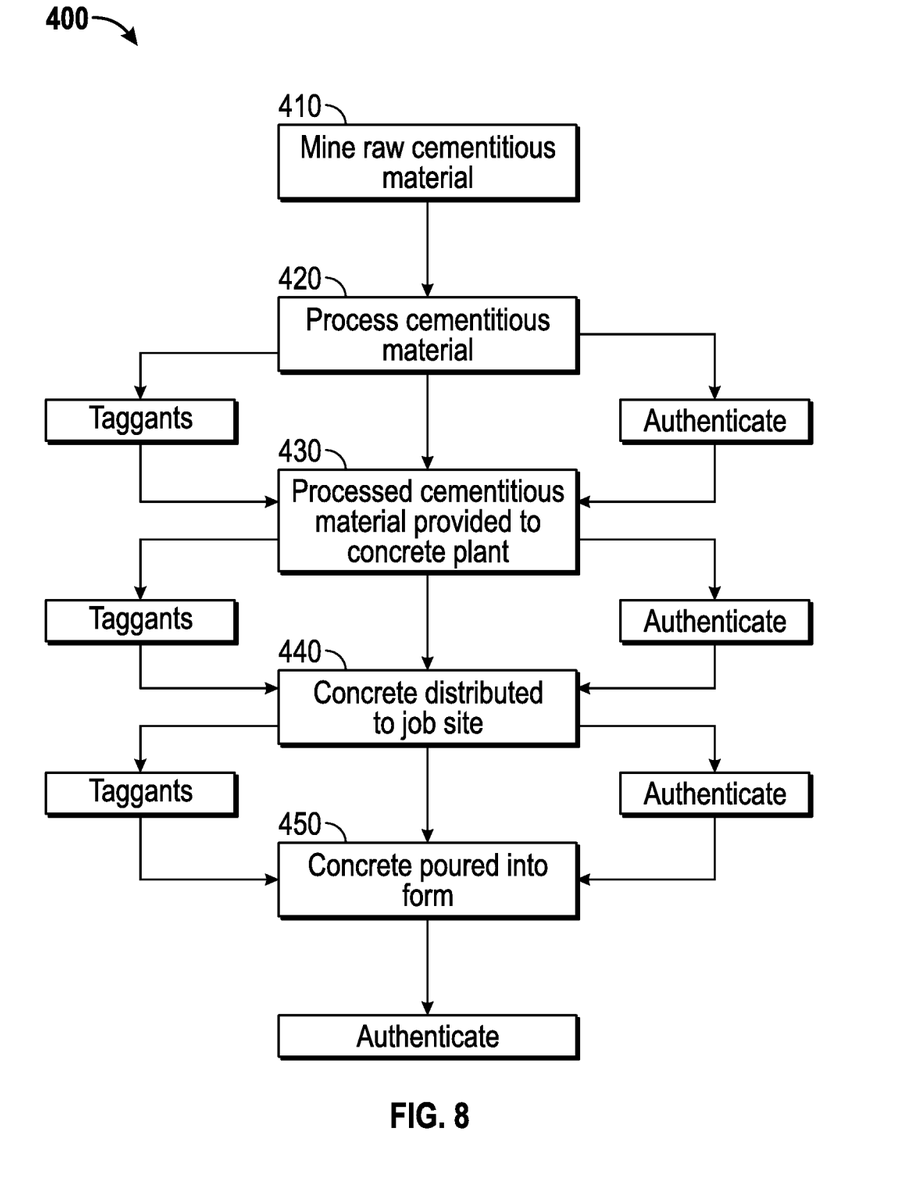
FIG. 8 is a flow diagram of a cement production process, according to one embodiment.

Referring next to the embodiment shown in FIG. 8, concrete is produced and distributed according to a process 400. As shown in FIG. 8, raw cementitious material is mined (410) and processed (e.g., milled, ground, etc.) at 420. The processed cementitious material may be provided to a concrete plant at 430. In some embodiments, additional materials (e.g., aggregates, reinforcement fibers, chemical admixtures, fly ash, sand, etc.) are mixed into the processed cementitious material by the concrete plant at 430. The mixed concrete is thereafter distributed to a jobsite (440). The mixed concrete may be distributed with concrete trucks to a remote jobsite or transported to an internal manufacturing facility (e.g., to produce pre-form concrete products). The distributed concrete is thereafter poured into a concrete form (450).

As shown in FIG. 8, taggants may be introduced into the cementitious material at a plurality of points within process 400. Taggants may be introduced after the raw cementitious material is processed between 420 and 430. Such taggants may include data relating to a characteristic of the cementitious material (e.g., processor's identity, processing date, etc.). The processed cementitious material is provided to a concrete plant at 430 where it may be authenticated before or after being mixed with additional materials (i.e. the cementitious material may be authenticated between 430 and 440). By way of example, a concrete plant may authenticate the processor, the processing date, the moisture content, or still another characteristic of the cementitious material to ensure that the concrete produced therefrom conforms with predetermined specifications (e.g., standards, customer requests, etc.). A processor may monitor a mix status of the concrete by evaluating a homogeneity of the taggants in the concrete mixture. The mix status may include whether the concrete has been mixed to a specified degree.

In some embodiments, taggants are introduced between 430 and 440 (e.g., to identify a production time, etc.) by the concrete plant or an inspector. The concrete is thereafter delivered to the jobsite at 440. The concrete may be authenticated by an inspector upon arrival or at another point before entering the concrete form (e.g., as the concrete flows down the concrete chute, etc.). Taggants may be added to the concrete between 440 and 450 (e.g., taggants specifying the area of the building where the concrete is intended to be placed). After the concrete is poured into the form at 450, the concrete may be authenticated (i.e. in-situ authentication) either before or after the concrete sets. In some embodiments, inspectors introduce taggants at various points throughout process 400 after the authentication process and before the following process (e.g., taggants relating to an authentication status of the cementitious material).

While various aspects and embodiments have been disclosed herein, other aspects and embodiments will be apparent to those skilled in the art. For example, elements shown as integrally formed may be constructed of multiple parts or elements. It should be noted that the elements and/or assemblies of the enclosure may be constructed from any of a wide variety of materials that provide sufficient strength or durability, in any of a wide variety of colors, textures, and combinations. Accordingly, all such modifications are intended to be included within the scope of the present inventions. The order or sequence of any process or method steps may be varied or re-sequenced according to other embodiments. The various aspects and embodiments disclosed herein are for purposes of illustration and are not intended to be limiting, with the true scope and spirit being indicated by the following claims.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data, which cause a general-purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps, and decision steps.

What is claimed is:

1. A traceable cement mixture, comprising:
a volume of cementitious material;
a plurality of taggants disposed within the volume of cementitious material according to a taggant mix ratio that is specified based on a quality of the cementitious material, the plurality of taggants including data relating to a characteristic of the volume of cementitious material; and
a volume of an additional material mixed with the volume of cementitious material according an additional material mix ratio.

2. The mixture of claim 1, wherein the characteristic includes at least one of a grade, a quality, a manufacturer, a manufacture date, an inspection status, an inspection date, and an approval status of the volume of cementitious material.

3. The mixture of claim 1, wherein the plurality of taggants comprise a hollow shell, the hollow shell configured to float within a volume of water.

4. The mixture of claim 1, wherein the plurality of taggants include a material that changes color when exposed to water.

5. The mixture of claim 4, wherein the material includes a water-sensitive dye.

6. The mixture of claim 4, wherein the material includes iron, and wherein oxidation or reduction of the material provides a color change.

7. The mixture of claim 1, wherein the additional material includes at least one of an aggregate, a reinforcement fiber, a chemical admixture, and a mineral admixture.

8. The mixture of claim 1, wherein the plurality of taggants are secured.

9. The mixture of claim 1, wherein the plurality of taggants include a material having fluorescent properties, the material configured to at least one of provide information and identify the taggant within a volume of concrete associated with the volume of cementitious material.

10. The mixture of claim 9, wherein the plurality of taggants have a maximum dimension of less than one millimeter.

11. The mixture of claim 1, wherein the plurality of taggants include a RFID device.

12. The mixture of claim 1, further comprising a second taggant.

13. The mixture of claim 1, wherein the taggant has a density that is substantially equal to a density of a volume of concrete associated with the volume of cementitious material.

14. The mixture of claim 1, wherein the taggant has a density that is substantially less than a density of the volume of cementitious material such that the taggant sinks upon hydration.

15. The mixture of claim 1, wherein the taggant has a density that is approximately equal to a density of the volume of cementitious material such that the taggant raises or sinks upon dilution.

16. A traceable cement mixture, comprising:
a volume of cementitious material;
a first taggant disposed within the volume of cementitious material, the first taggant including data relating to a first characteristic of the volume of cementitious material; and
a second taggant disposed within the volume of cementitious material, the second taggant including data relating to a second characteristic of the volume of cementitious material different than the first characteristic, wherein the first taggant includes data that is different than the data of the second taggant.

17. A traceable cement mixture, comprising:
a volume of cementitious material; and
a taggant disposed within the volume of cementitious material, the taggant including data relating to a characteristic of the volume of cementitious material,
wherein the characteristic includes a number density of taggants within the volume of cementitious material, the number density of taggants specified based on a quality of the cementitious material.

* * * * *